US009700347B2

(12) United States Patent
Shiber

(10) Patent No.: US 9,700,347 B2
(45) Date of Patent: *Jul. 11, 2017

(54) ADAPTIVE ROTARY CATHETER FOR OPENING OBSTRUCTED BODILY VESSELS

(76) Inventor: Samuel Shiber, Santa Barbara, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 14/238,983

(22) PCT Filed: Aug. 14, 2012

(86) PCT No.: PCT/US2012/050759
§ 371 (c)(1),
(2), (4) Date: Feb. 14, 2014

(87) PCT Pub. No.: WO2013/025697
PCT Pub. Date: Feb. 21, 2013

(65) Prior Publication Data
US 2014/0200599 A1 Jul. 17, 2014

Related U.S. Application Data

(60) Provisional application No. 61/575,289, filed on Aug. 17, 2011, provisional application No. 61/686,864, filed on Apr. 13, 2012.

(51) Int. Cl.
*A61B 17/3207* (2006.01)
*A61M 1/00* (2006.01)
(Continued)

(52) U.S. Cl.
CPC ..... *A61B 17/320758* (2013.01); *A61M 1/008* (2013.01); *A61B 2017/22048* (2013.01);
(Continued)

(58) Field of Classification Search
CPC .......... A61B 17/3207; A61B 17/32075; A61B 17/320758; A61B 2017/320716;
(Continued)

(56) References Cited

U.S. PATENT DOCUMENTS 4,091,880 A * 5/1978 Troutner ............ A61B 17/1628
173/170
4,732,154 A * 3/1988 Shiber .............. A61B 17/22012
606/108
(Continued)

FOREIGN PATENT DOCUMENTS

| GB | 2426456 | 11/2006 |
|---|---|---|
| WO | WO98/30928 | 9/1998 |
| WO | WO99/02542 | 5/1999 |

OTHER PUBLICATIONS

International Search Report mailed Oct. 23, 2012; PCT/US12/50759.
(Continued)

*Primary Examiner* — David C Eastwood
(74) *Attorney, Agent, or Firm* — Lynne M. Blank, Esq.

(57) ABSTRACT

A rotary catheter for opening partially and totally obstructed bodily vessels of varying diameter (e.g., blood vessel) which comprises a motor-driven flexible hollow shaft rotatably disposed in a flexible tube, an aspiration channel defined between the flexible tube and the hollow shaft, a tip affixed to a distal end of the hollow shaft having a rounded distal end being rotatable and slideable over the guidewire, the tip having sides, a base and a crown that is offset away from a longitudinal axis of the hollow shaft further than the base and a distance between the sides being smaller than a distance between the crown and the base leaving open passages along the tip, the guidewire can be withdrawn proximally to allow the rotating crown to displace the distal end of the tip away from said wall of said vessel to tunnel through a total obstruction.

19 Claims, 9 Drawing Sheets

(51) Int. Cl.
  *A61B 17/22* (2006.01)
  *A61B 90/00* (2016.01)
(52) U.S. Cl.
  CPC ............. *A61B 2017/22068* (2013.01); *A61B 2017/22071* (2013.01); *A61B 2017/320766* (2013.01); *A61B 2090/08021* (2016.02)
(58) Field of Classification Search
  CPC ....... A61B 2017/320733; A61B 2017/320741; A61B 2017/320766; A61B 2017/320775; A61B 2019/481; A61M 1/008
  See application file for complete search history.

(56) References Cited

U.S. PATENT DOCUMENTS

| | | | | |
|---|---|---|---|---|
| 4,819,634 A | * | 4/1989 | Shiber | A61B 17/320758 604/95.01 |
| 4,842,579 A | * | 6/1989 | Shiber | A61B 17/22012 604/22 |
| 4,883,458 A | * | 11/1989 | Shiber | A61B 8/12 604/22 |
| 4,886,490 A | * | 12/1989 | Shiber | A61B 8/12 604/22 |
| 4,894,051 A | * | 1/1990 | Shiber | A61B 17/22012 604/22 |
| 4,990,134 A | * | 2/1991 | Auth | A61B 17/22031 604/22 |
| 5,002,553 A | * | 3/1991 | Shiber | A61B 17/22012 604/22 |
| 5,007,896 A | * | 4/1991 | Shiber | A61B 17/22012 604/22 |
| 5,030,213 A | | 7/1991 | Rumberger | |
| 5,042,984 A | * | 8/1991 | Kensey | A61B 17/320758 606/128 |
| 5,116,350 A | | 5/1992 | Stevens | |
| 5,135,531 A | * | 8/1992 | Shiber | A61B 8/12 606/159 |
| 5,306,244 A | * | 4/1994 | Shiber | A61B 8/12 600/585 |
| 5,334,211 A | * | 8/1994 | Shiber | A61B 8/12 604/22 |
| 5,653,696 A | | 8/1997 | Shiber | |
| 5,681,336 A | * | 10/1997 | Clement | A61B 17/320758 604/96.01 |
| 5,806,404 A | | 9/1998 | Sher | |
| 6,129,734 A | * | 10/2000 | Shturman | A61B 17/320758 604/22 |
| 6,143,009 A | * | 11/2000 | Shiber | A61B 17/320758 606/159 |
| 6,258,052 B1 | | 7/2001 | Milo | |
| 6,416,523 B1 | * | 7/2002 | Lafontaine | A61B 17/320758 600/373 |
| 6,440,148 B1 | * | 8/2002 | Shiber | A61B 8/12 606/159 |
| 6,482,215 B1 | * | 11/2002 | Shiber | A61B 17/320758 606/159 |
| 6,572,630 B1 | * | 6/2003 | McGuckin, Jr. | A61B 17/320758 606/159 |
| 6,758,851 B2 | | 7/2004 | Shiber | |
| 7,316,697 B2 | * | 1/2008 | Shiber | A61B 17/320758 606/159 |
| 8,137,369 B2 | * | 3/2012 | Shturman | A61B 17/320725 606/159 |
| 8,236,016 B2 | * | 8/2012 | To | A61B 17/320758 606/159 |
| 8,795,306 B2 | * | 8/2014 | Smith | A61B 17/320758 604/525 |
| 2002/0007190 A1 | * | 1/2002 | Wulfman | A61B 17/320725 606/167 |
| 2002/0029056 A1 | * | 3/2002 | Hall | A61B 17/320758 606/170 |
| 2002/0151918 A1 | * | 10/2002 | Lafontaine | A61B 17/3207 606/159 |
| 2002/0165567 A1 | * | 11/2002 | Shiber | A61B 17/320758 606/159 |
| 2002/0188276 A1 | * | 12/2002 | Evans | A61B 17/22 604/509 |
| 2003/0028206 A1 | * | 2/2003 | Shiber | A61B 17/320758 606/159 |
| 2004/0006358 A1 | * | 1/2004 | Wulfman | A61B 5/061 606/167 |
| 2005/0119615 A1 | | 6/2005 | Noriega | |
| 2008/0004646 A1 | * | 1/2008 | To | A61B 17/32075 606/159 |
| 2008/0306498 A1 | * | 12/2008 | Thatcher | A61B 17/320758 606/159 |
| 2009/0005755 A1 | | 1/2009 | Keith | |
| 2009/0069829 A1 | * | 3/2009 | Shturman | A61B 17/320725 606/159 |
| 2009/0149877 A1 | * | 6/2009 | Hanson | A61B 17/320758 606/159 |
| 2010/0121361 A1 | * | 5/2010 | Plowe | A61B 17/320758 606/159 |
| 2010/0292720 A1 | * | 11/2010 | Thatcher | A61B 17/320758 606/159 |
| 2011/0152907 A1 | * | 6/2011 | Escudero | A61B 17/320758 606/159 |
| 2012/0172905 A1 | * | 7/2012 | Lee Shee | A61B 17/1671 606/180 |
| 2013/0103046 A1 | * | 4/2013 | Shiber | A61B 17/320758 606/127 |
| 2014/0200599 A1 | * | 7/2014 | Shiber | A61B 17/320758 606/159 |
| 2015/0094733 A1 | * | 4/2015 | Shiber | A61B 17/320758 606/127 |
| 2015/0164541 A1 | * | 6/2015 | Shiber | A61B 17/320758 604/28 |

OTHER PUBLICATIONS

International Search Report, Jun. 27, 2011, PCT/US11/031197.
Supplemental European Search Report, Jun. 24, 2014, EP11777774.

\* cited by examiner

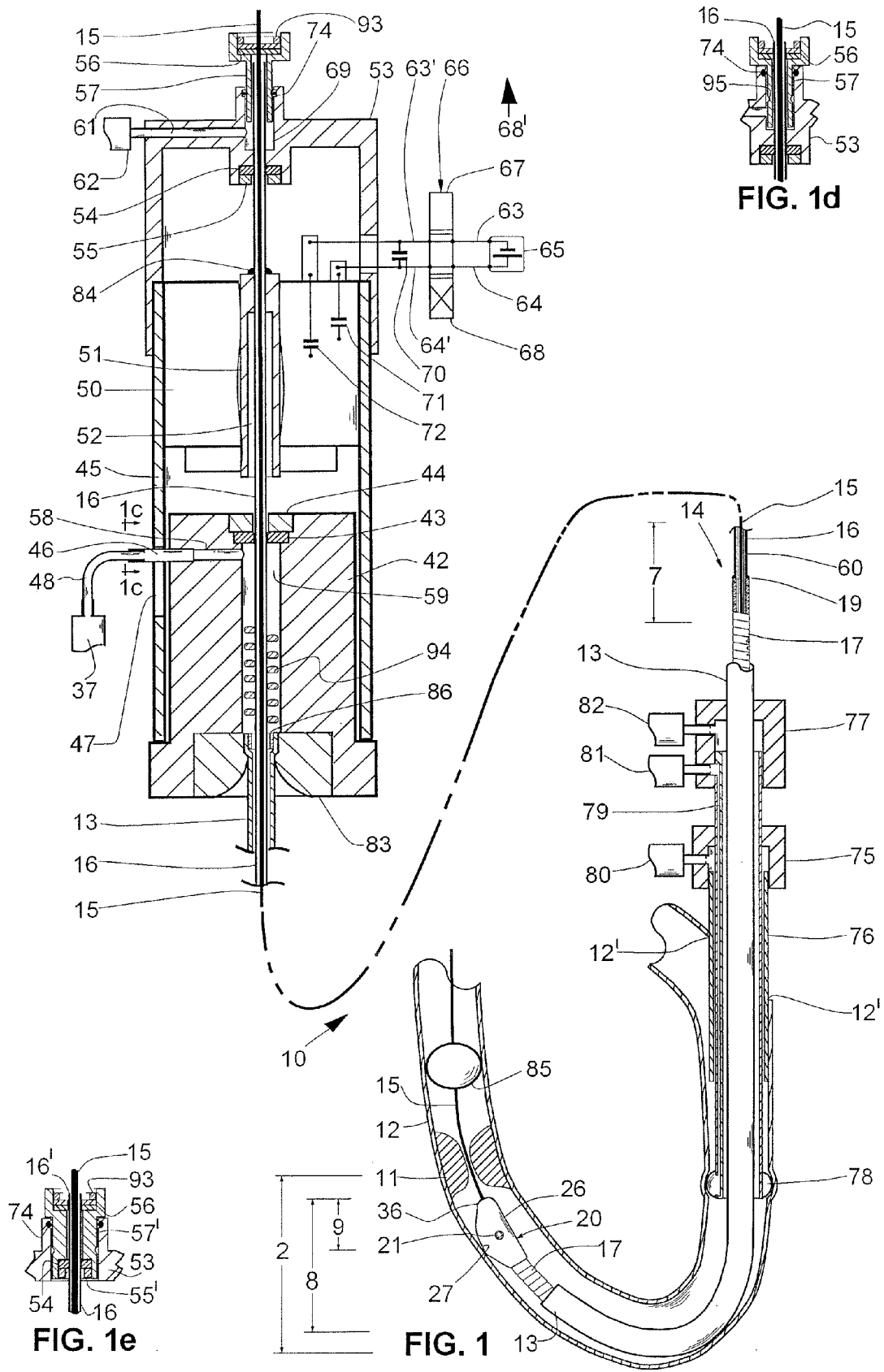

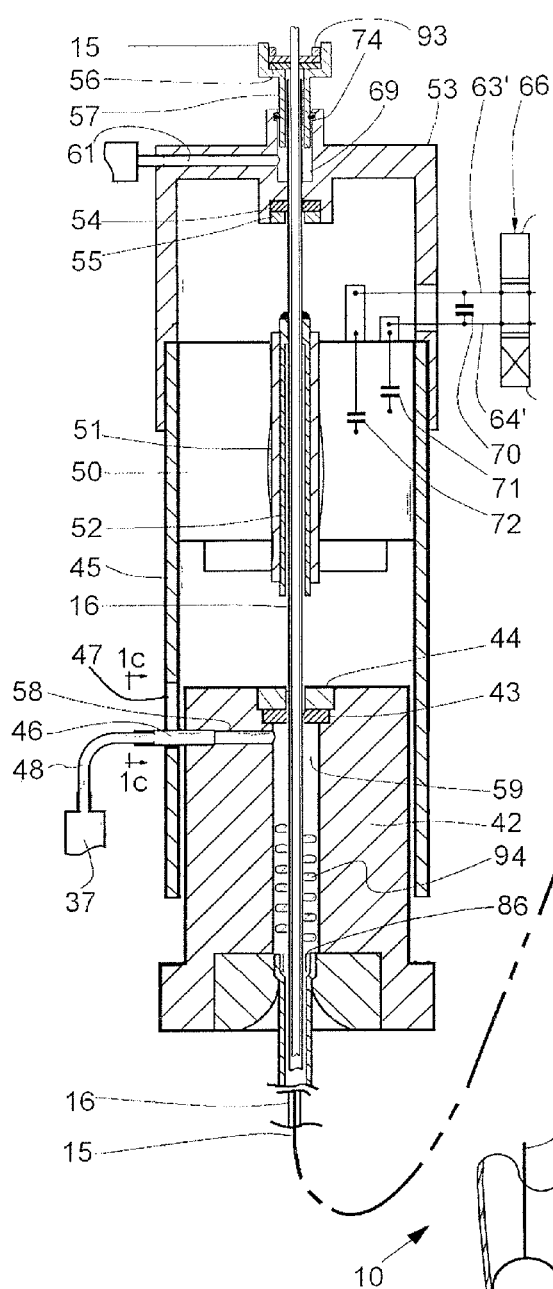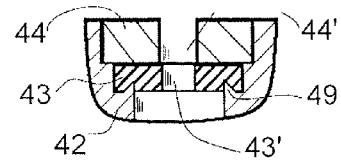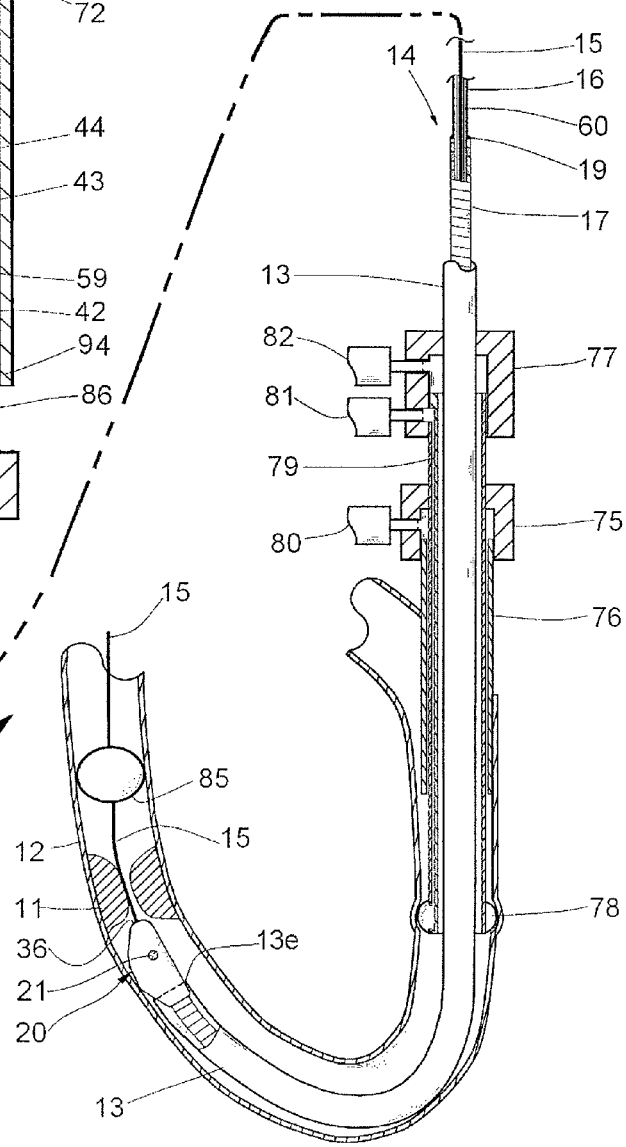
FIG. 1b
FIG. 1c
FIG. 1a

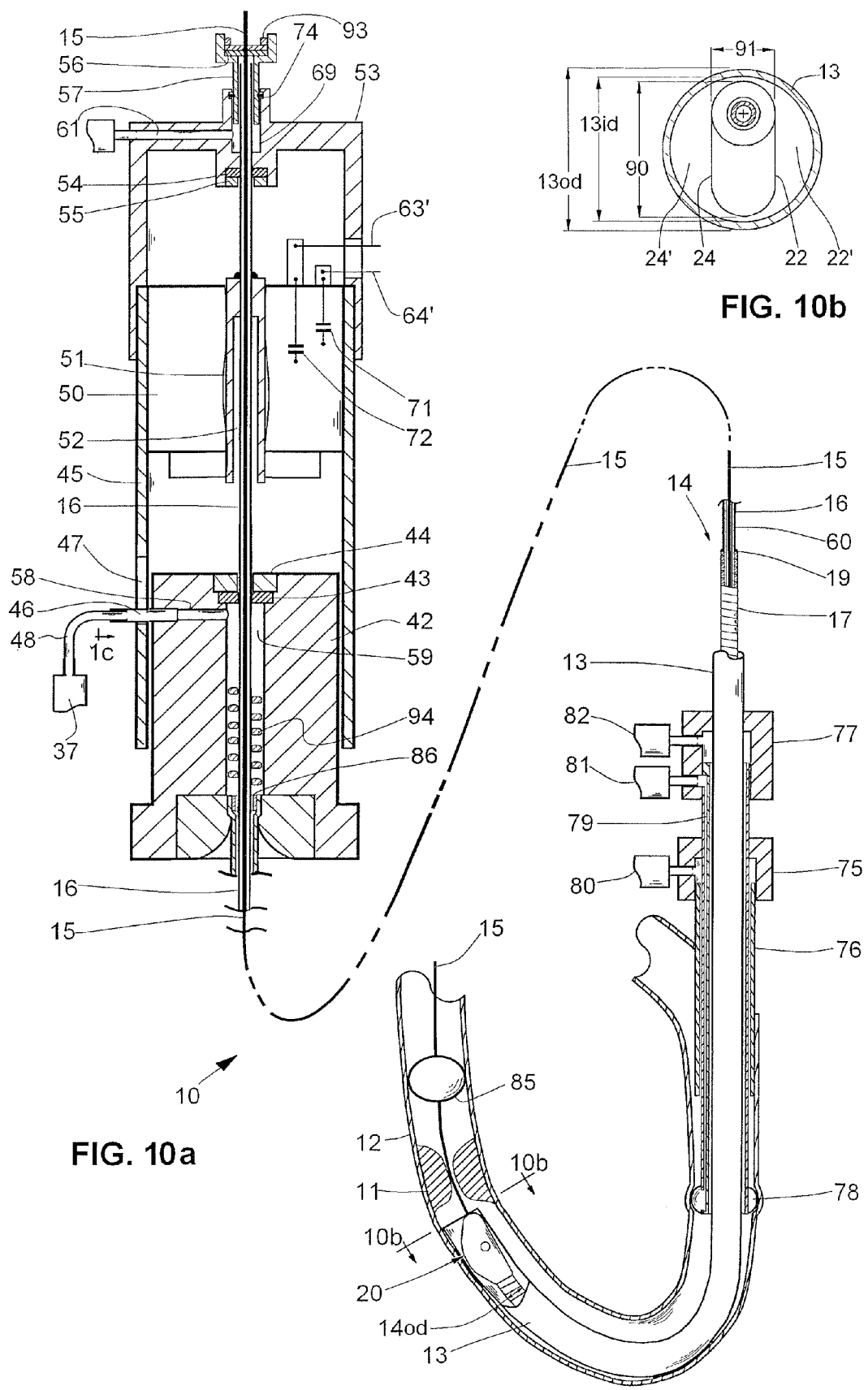

ADAPTIVE ROTARY CATHETER FOR OPENING OBSTRUCTED BODILY VESSELS

This application relates to a rotary catheter for opening partially, and totally obstructed bodily vessels, such as blood vessels, of varying diameters.

Prior pharmacological, surgical and transcatheter device approaches for opening obstructed blood vessels can be slow, traumatic and expensive. Furthermore, since the diameter and the nature of a long obstruction is likely to vary along the diseased vessel and since a typical prior art device is usually capable of treating a narrow range of vessel diameters and a certain type of obstruction, multiple sizes and different kinds of prior art devices may be needed in a single case. Thus, it is an object of the present invention to provide a safe, simple and effective rotary catheter that readily adapts to dealing with partial and/or total obstructions in a wide range of vessel diameters.

For example, a number of prior art devices comprise an abrasive tip, with a spherical cross section, mounted on a rotating shaft designed to specifically grind hard obstructions to very small particles. Due to the small size of the particles these devices have to be rotated at high speeds (e.g., 200,000 revolutions per minute) to grind the entire obstruction material in a reasonable time. In some of these devices the tip is eccentrically mounted on the shaft and some of these devices use aspiration to try and remove the particles. However, as the abrasive tip of these devices grinds through a small vessel, or through a hard obstruction material, even if the tip is mounted eccentrically on the shaft it is forced to rotate in an opening that is not larger than the tip, which the tip essentially blocks. This prevents aspiration and cooling fluid from reaching the distal surface of the tip which may lead to embolization and quickly cause thermal injury and/or perforation of the vessel's wall.

In contrast, the present invention utilizes a tip, with a narrowed cross section defined between two sides, whose primary mode of operation is to bluntly impact the obstruction material with one of these sides. The tip also has a base and a smooth crown that is adapted to atraumatically slide against the vessel's wall. However it should be noted that vascular obstructions may become integrated with the wall of the vessel and depending on the nature of the obstruction and the shape of the remaining lumen (if any) the tip, with its narrowed cross section, can also be used to penetrate and radially displace such an obstruction as it rotates. Passages defined by and along the sides of the tip connect the distal and the proximal areas of the tip and allow fluid (e.g., blood or irrigating fluid comprising saline) to lubricate the vessel or the tunnel and prevent it from becoming dry and overheated while the tip rotates, and it also allows aspiration to reach the distal end of the rotating tip and remove particles and fluid.

An embodiment according to the present invention, which is discussed in more detail hereinafter, comprises a motor-driven flexible hollow shaft whose distal portion is preferably made of a spiraled wire with a tip affixed to its distal end. The hollow shaft is rotatably disposed in a flexible tube and an aspiration channel is defined between an internal diameter of the flexible tube and an external diameter of the hollow shaft. A distal portion of the hollow shaft is free to move radially in the aspiration channel enabling the aspiration channel to ingest particles which are smaller than a difference between the internal and external diameters. Relative motion between the radially moving and rotating hollow shaft and the flexible tube eases movement of the particles through the aspiration channel and impedes the particles from clogging the aspiration channel. A non-abrasive tip with a narrowed cross section (as compared to a round cross section) is affixed to a distal end of the hollow shaft. The tip has a rounded atraumatic (i.e., less likely to injure a wall of the vessel) distal end which defines a bore adapted to fit over a guidewire and the hollow shaft and the tip are rotatable and slideable over the guidewire. The tip, which is extended out of a distal end of the flexible tube to enhance its engagement with the obstruction material, has a first side adapted to impact the obstruction when it is rotates in a first direction and it has a second side. The tip also has a base and an opposing smooth crown that is offset away from a longitudinal axis of the hollow shaft further than the base is offset away from the longitudinal axis enlarging the area that the tip can sweep when rotating in a larger vessel.

A distance between the sides is smaller than the distance between the crown and the base, leaving open aspiration passageways along the sides even when the tip is inside the flexible tube, a small vessel or when it is tunneling through a hard obstruction. The narrowness of the tip also enables it to enter into narrow obstructions and widen them as it rotates.

Total occlusions often prevent the delivery of percutaneous trans-catheter treatment forcing a patient to undergo a more formidable bypass surgery. Upon encountering a total obstruction that can not be crossed with the guidewire the rotary catheter can be advanced to the obstruction and then the guidewire is withdrawn proximally into the hollow shaft past the distal end of the tip adapting the system to cross the total occlusion. As the tip is rotated its smooth crown atraumatically slides against the vessel's wall and displaces a distal end of the tip away from the wall, directing the tip to tunnel through the obstruction. Once the obstruction is crossed, the guidewire can be advanced distally past the tip to provide guidance and support to the rotary catheter.

The rotary catheter can be inserted into the vessel directly, e.g., when access to a vessel is gained surgically, or through the skin via an introducer. The introducer can also be used to inject fluids (e.g., a mixture comprising saline, heparin and a contrast agent) into the vessel which, together with blood, keeps the obstruction particles suspended so that they can be readily aspirated. An optional guiding catheter can be used when the rotary catheter has to be guided further into the vessel. The guiding catheter can incorporate a proximal embolic barrier for temporarily blocking flow through the vessel, while the rotary catheter macerates and aspirates the obstruction material, thereby reducing the likelihood of releasing particles downstream. A distal embolic protection device can also be employed for the same purpose and, when the rotary catheter is used in a limb, an external pressure cuff can be utilized to temporarily stop circulation in the affected vessels to allow the rotary catheter to safely macerate and aspirate the particles and fluid in which they are suspended. A passageway, defined through the rotary catheter housing, connects the aspiration channel with an external port so that the port can be utilized to aspirate fluids and particles from the vessel.

To prevent the flexible tube from kinking (i.e., diametrically collapsing) and to prevent the hollow shaft from being sharply bent at the point in which they are connected to the housing, their radius of bending is limited to a radius of curvature of a wall of a depression defined by the housing area that surrounds the flexible tube. The rotary catheter can be manufactured in varying lengths and diameters to reach and treat different anatomical locations and different forms of obstructions, as well as to suit users' preferences.

BRIEF DESCRIPTION OF THE DRAWINGS

FIG. 1 shows a motorized rotary catheter, according to the present invention, with a motor-driven flexible hollow shaft having a tip affixed to its distal end. The hollow shaft and the tip are rotatably and slideably disposed in a flexible tube with an aspiration channel defined between them. The tip, which is shown extended out of a distal end of the flexible tube, and the hollow shaft are rotatable and slideable over the guidewire which extends distally beyond a distal end of the tip. ("distal" or "distally" refers to a location or a direction further into the vessel and "proximal" or "proximally" means the opposite);

FIG. 1a shows the rotary catheter with the distal end of its flexible tube slid close to the tip to reduce a gap between them and impede an edge of the flexible tube from engaging with a wall of the vessel while the rotary catheter is advanced distally in the vessel towards an obstruction;

FIG. 1b shows enlargement of a rotary seal of the rotary catheter;

FIG. 1c shows cross-sectional enlargement of a connection between a ferrule and flexible tube viewed on a plane 1c-1c marked on FIG. 1a;

FIG. 1d is cross-sectional view of a proximal seal mechanism shown in an open-position (the proximal seal is shown, as a part of the embodiment depicted in FIG. 1, in a closed-position);

FIG. 1e is cross-sectional view of a double proximal seal mechanism shown in an open-position.

FIG. 10 shows an overview of a modified rotary catheter wherein the flexible tube can be optionally moved distally over the tip to shield it as shown in FIG. 10a;

FIG. 10b shows an end view of the rotary catheter as viewed on a plane 10b-10b marked on FIG. 10a;

Figure 2:
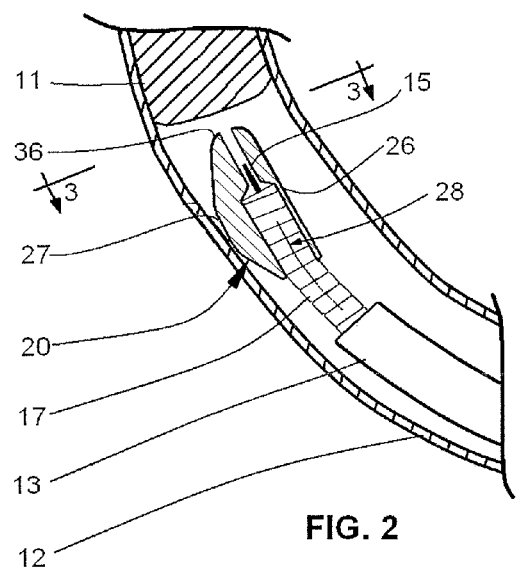
FIG. 2 shows an enlargement of a region marked 2 on FIG. 1 where the vessel is totally occluded and the guidewire withdrawn proximally beyond the distal end of the tip allowing the rotating crown, as it slides against the wall of the vessel, to displaces the distal end of the tip away from the wall of the vessel.

The middle portions of the embodiments shown in FIGS. 1, 1a, 10, 10a, 11, and 12 are represented by phantom lines due to space limitations on the drawing sheets.

DETAILED DESCRIPTION OF THE EMBODIMENTS

FIG. 1 shows a motorized rotary catheter 10, according to the present invention, for opening an obstruction 11 (e.g., thrombus; atheroma) in a bodily vessel 12 (e.g., a blood vessel).

Figure 4:
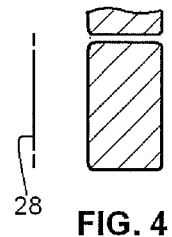
FIGS. 4, 5 and 6 show examples of cross sections of flattened wires that can be used to wind a spiraled wire.
Figure 5:
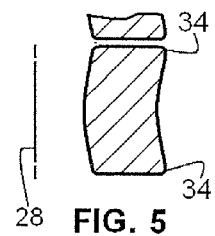
Figure 6:
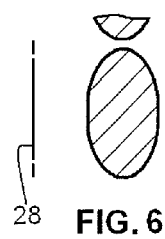

The rotary catheter 10 comprises a motor-driven flexible hollow shaft 14, rotatably disposed in a flexible tube 13 that is preferably made of thin plastic material. A proximal portion 16 of the hollow shaft is preferably a thin-walled tube and a distal portion of the hollow shaft 17 is preferably made of a spiraled wire. The wire that is used to wind the spiraled wire preferably has a flattened cross-section (such a cross section can be obtained by taking a standard round wire and running it between rollers that squeeze and flatten it, please note FIGS. 4-6). The hollow shaft portions 16 and 17 are preferably made of metal (e.g., stainless steel; Nitinol) and are connected together, for example, by a circumferential weld 19 (please note FIG. 1) or by two circumferential welds 24 and 25 and a reinforcing sleeve 30 (please note FIG. 7.)

Figure 9:
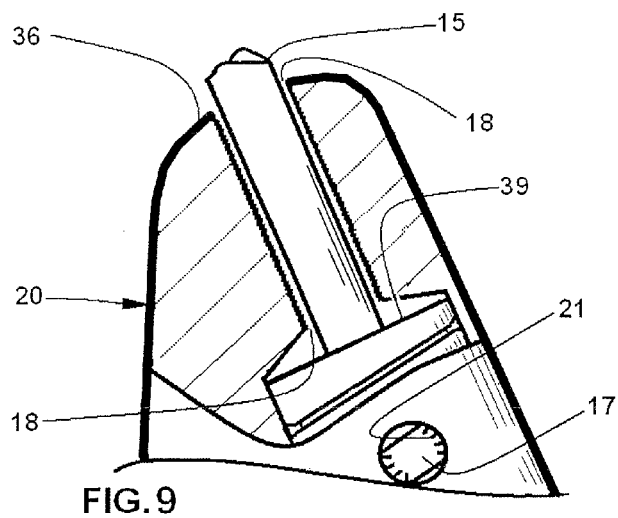
FIG. 9 shows an enlarged cross section of a distal end of the tip marked 9 on FIG. 1.

A tip 20 is affixed by preferably a laser weld 21 to a distal end of the spiraled wire (please note FIG. 9) so that the hollow shaft 14 and the tip 20 are rotatable and slideable over a guidewire 15. The weld is at a point along the spiraled wire that is nested inside the tip where the weld is subjected primarily to shearing loads but is otherwise protected. The tip has a first side 22 for impacting the obstruction as the hollow shaft is rotated in a first direction 40. A second side 24 can be used to impact the obstruction if the hollow shaft is rotated in a second direction 41 (please note FIG. 3.)

The tip also has a base 26 and an opposing smooth crown 27 that is adapted to atraumatically slide against a wall of the vessel without injuring it. An offset 89 of the crown ("offset" refers to a distance from the longitudinal axis 28 of the spiraled wire 17) is larger than an offset of the base 88 (the sum of offsets 88 and 89 equals to the height of the blade 90.) As the tip rotates around the axis 28 the crown slides along the circumference of a vessel or a hypothetical tunnel (marked with a phantom line 29) that the tip opens (please note FIG. 3) which is substantially larger than a tunnel (marked with an interrupted line 35) that a hypothetical tip of equal height, which is symmetrically mounted onto the spiraled wire (i.e. offset 88 equals offset 89) would have theoretically opened. It should however be understood that the actual cross-sectional area of the tunnel that the tip 20 opens may increase due to, for example, dynamic forces affecting the tip (e.g., centrifugal force) or the actual cross-sectional area may decrease when, for example, the tip operates in a smaller vessel or it tunnels through a hard obstruction.

The tip 20 has a narrowed cross-section with a width 91 that is smaller than its height 90 (please note FIG. 3) which reduces the size and circumference of its cross-section relative to a round tip whose diameter equals the height 90. This smaller circumference requires a smaller opening in the wall of the vessel for inserting the tip into the vessel. The narrowed cross-section also enhances the tip's ability to fit into a narrow opening in a hard obstruction and to widen it as the tip rotates. The tip's narrowed cross-section also leaves open passageways 22' and 24' along its sides 22 and 24, respectively. These passageways enable aspiration from the distal end of the flexible tube 13 to reach particles that are distal to the tip even when the tip is operating in a small vessel or tunnel with a diameter as small as the height 90. As the particles and fluid in which they are suspended pass through passageways 22' and 24', over the rotating tip, they become further macerated and are readily aspirated through the tube into a syringe 37 as discussed below.

Figure 8A:
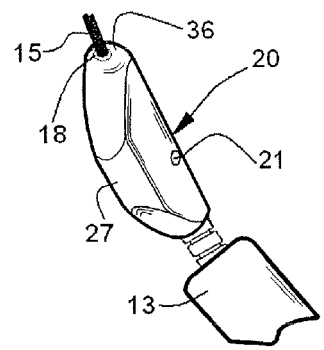
FIG. 8a shows a perspective view of the tip.
Figure 8:
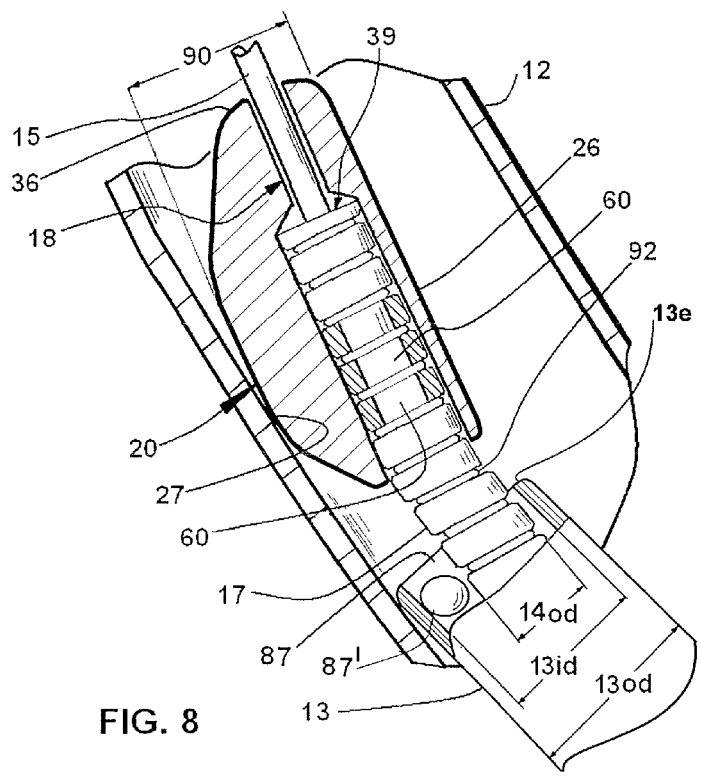
FIG. 8 shows an enlarged cross section of a tip area marked 8 on FIG. 1.

A distal rounded end 36 of the tip 20 covers a distal end of the spiraled wire 39 and defines a bore 18 (please note FIGS. 8 and 9) which rotatably and slideably fits over the guidewire enabling the guidewire to support and guide the tip. A close fit between bore 18 and the guidewire restricts blood flow through the bore 18 and the amount of residue that enters and deposits in the bore 18 and around the guidewire.

As shown in FIG. 1 the flexible tube 13 is affixed (e.g., bonded and/or press fitted, and radially supported internally by a ferrule 86, to a strain relief 83 which is affixed to a cylinder 42 which also houses a seal 43. The outer periphery of the seal 43 is tightly pressed by a bushing 44 against a circular ridge 49 forming a peripheral static seal (the ridge is shown in the enlarged view FIG. 1b.) A bore 44' in the bushing acts as a bearing which offsets the hollow shaft portion 16 to the extent that is needed to align it to rotate concentrically relative to a bore 43' which is formed through the seal 43 (such a combination of a seal and an adjacent concentric bearing are referred to hereinafter as a "seal set".) This forced concentricity on the one hand nulls the effect of the cumulative eccentricities contributed by parts numbers 42, 45, 50, 51, 83 and the hollow shaft portion 16, which in turn reduces the interference fit needed between the bore 43' and the hollow shaft portion 16 to maintain a rotary seal between them and thereby it reduces frictional power loss in the seal. On the other hand it also eases the tolerances that the parts 42, 45, 50, 51 and hollow shaft portion 16 have to be manufactured to and thereby it lowers the manufacturing costs of the rotary catheter.

The cylinder 42 is slidingly disposed in a distal end of a tubular housing 45 and a ferrule 46, that is press-fitted into the cylinder 42, is slidingly disposed in an elongated slot 47 defined in the housing 45. This allows the cylinder 42 to be slid proximally into the housing (as shown in FIG. 1) or to be slid distally (as shown in FIG. 1a) displacing the distal end of the flexible tube 13 relative to the tip 20.

A flexible conduit 48, the ferrule 46, bores 58 and 59, and seal 43 (please note FIG. 1) define together a hydraulic connection between a proximal end of the flexible tube 13 and a suction means in the form of the evacuated syringe 37 for aspirating particles of the obstruction and fluid in which they are suspended (only the front end of the syringe is depicted however syringes and vacuum syringes are commercially available from, for example, Merit Medical Systems, South Jordan, Utah.) The relative motion between the flexible tube 13 and the rotating hollow shaft 14 assists with the aspiration process by reducing the frictional resistance that these particles encounter while moving proximally in the flexible tube 13.

An optional helical wire 94 can be rotatably disposed in bore 59 and affixed to the hollow shaft portion 16. Upon rotation helical wire 94 automatically assists in moving fluid and particles proximally, but when not rotating, it resists such flow.

A small direct current motor 50 is housed in a proximal end of the housing 45, however, other types of electric or air-driven motors, and the like, can be used. The motor has a tubular output shaft 51 with an optional electrically insulating coating (not shown.) The shaft 51 is power transmittingly connected, through its proximal end, to the hollow shaft portion 16, by a circumferential weld 84 (or, alternatively, by epoxy which is not shown), leaving the length of hollow shaft portion 16 that is nested in a clearance 52 free to bend towards bore 44'. The increased length of hollow shaft portion 16 that participates in the bending towards bore 44' lowers the stress and strain in the hollow shaft and the frictional forces that develop in the bore 44' while the hollow shaft portion 16 rotates.

Figure 7:
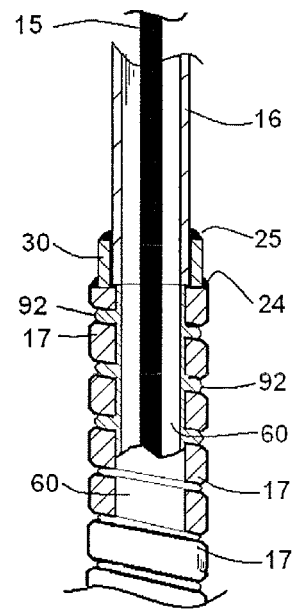
FIG. 7 shows an enlargement of a portion of the hollow shaft, marked 7 on FIG. 1, showing an optional reinforced welded connection.
Figure 10:
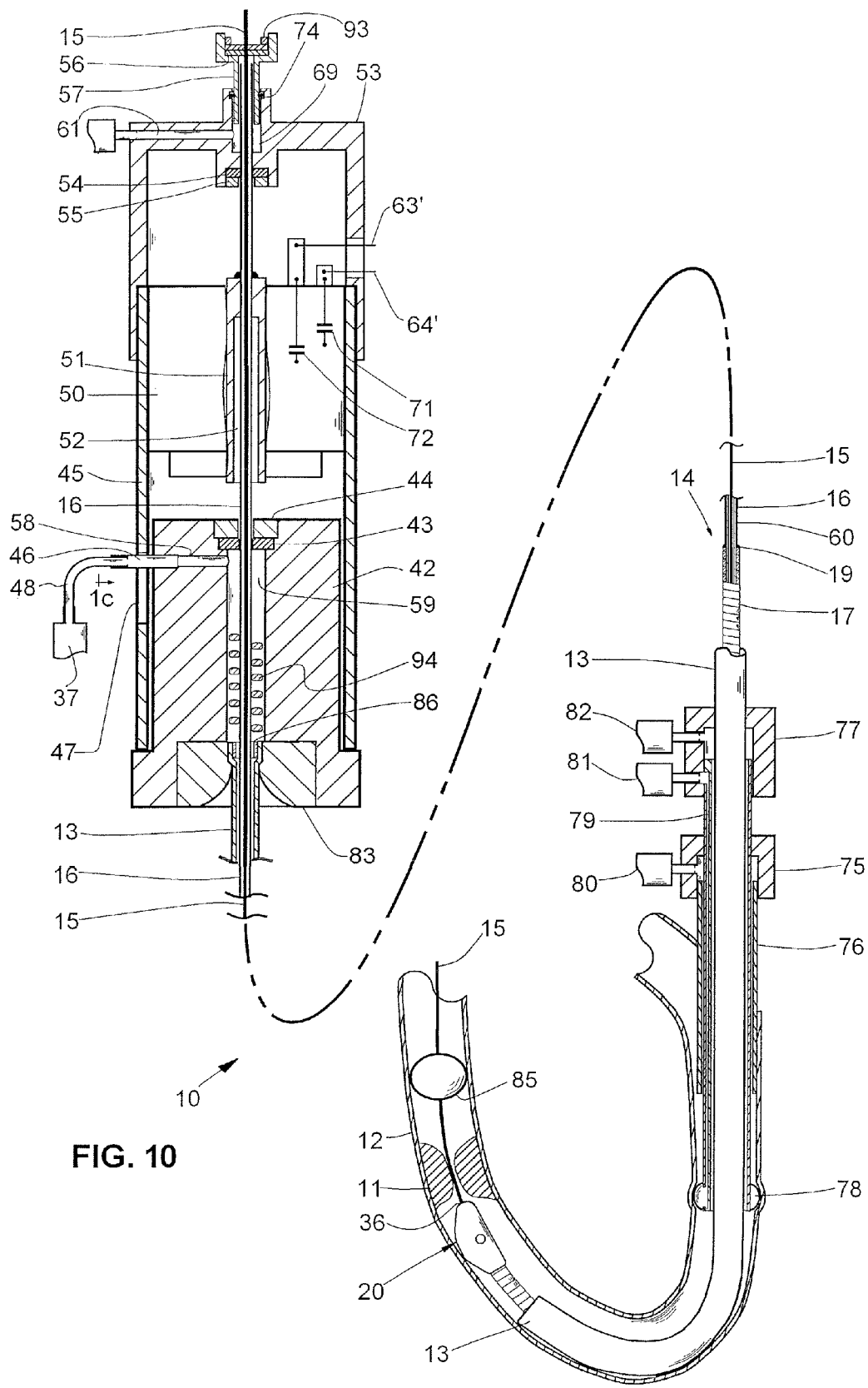

FIG. 7 shows the hollow shaft portion 16 connected and bonded to an optional flexible guidewire-liner 60 made of a thin-walled plastic tube. The liner may also be secured to the spiraled wire 17 with a spiraled protrusion 92 formed thereon. The spiraled wire can be wound of one or more wires (also referred to, in commercial terminology, as strands or filaments) and it can be constructed in one or more layers of wound wires (e.g., single and multi layered spiraled wires that are disclosed in my U.S. Pat. Nos. 4,819,634 and 5,007,896 issued on Apr. 11, 1989 and Apr. 16, 1991, respectively, which are incorporated herein by reference.) These earlier patents also show other optional spiraled wire designs such as a jagged spiraled wire shown in FIGS. 3 and 4 of my U.S. Pat. No. 5,007,896. Torque-transmitting flexible tubes utilizing a single or multilayered construction where each layer is made of one or more wires, are also commercially available from Asahi Intecc Co. (with offices at 2500 Red Hill Ave, Santa Ana, Calif., USA and at Aichi-ken, Japan.) The common feature of these and other suitable spiraled wires, as the term is used in this application, is their hollow design which allows them to slide and rotate over a guidewire coupled with an ability to transmit torque and their increased flexibility as compared with a standard tube of similar dimensions.

Referring back to FIG. 1, a proximal cap 53 houses a seal set comprising a seal 54, which seals around the hollow shaft portion 16, and a bushing 55 which secures it in place, and which like the bushing 44, also serves as a bearing that keeps the hollow shaft portion 16 rotating concentrically relative to the seal 54 with the beneficial effects discussed above in connection with the bushing 44 and the seal 43. The cap 53 also defines a bore containing an O-ring seal 74 through which a sliding housing means in the form of a stepped tube 57 is slidingly disposed. A seal 56 is secured in the stepped tube 57 by a ring 93. To enable insertion of the guidewire 15 thru the rotary catheter 10 the stepped tube 57 is pushed distally causing a proximal end 16' of the proximal hollow shaft portion 16 to cross the seal 56 (please refer to FIG. 1d) and enable the guidewire to freely pass thru the seal 56 into, or out of, the proximal end 16'. Upon pulling the stepped tube 57 proximally (please refer to FIG. 1) the seal 56 closes and seals around the guidewire 15. The seal 56 may be made of more than one layer of elastomeric material (e.g., two layers of flat silicone rubber) where the distal layer defines a round bore that tightly, yet slidingly, fits around the guidewire 15 and the proximal layer has a slit, or intersecting slits, that seal hermetically in the absence of the guidewire. The O-ring 74 seals around the stepped tube 57 frictionally prevents it from rotating and it also provides the user a tactile indication, when it drops into an undercut 95 (please note FIG. 1d), that the stepped tube 57 is sufficiently extended for the seal 56 to seal around guidewire 15.

FIG. 1e is cross-sectional view of a modified sliding housing means in the form of a stepped tube 57' which defines a bore that provides a bearing support and concentric alignment for the hollow shaft portion 16 with both seals 54 and 56 that are housed and secured at the distal and proximal ends of the stepped tube 57', respectively (therefore the bore of bushing 55' can be enlarged.) Stepped tube 57' is depicted being pushed distally to a position that enables the guidewire to freely pass distally or proximally thru the distal end 16'. Upon pulling the stepped tube 57' proximally the seal 56 closes and, if a guidewire is present, seals around the guidewire. In this modified configuration shown in FIG. 1e the O-ring 74 provides anti-rotational friction and tactile indication discussed above, but it does not have to act as a seal.

A syringe 62 is hydraulically connected to a proximal end the hollow shaft portion 16 through a passage 61 and a bore 69 defined in the cap 53. The syringe 62 can be used to introduce a fluid mixture (e.g., a mixture of saline and heparin) into the hollow shaft portion 16 and into the liner 60 to prevent blood from entering and clotting in the liner and in the hollow shaft portion 16. Immersion of the proximal end of hollow shaft portion 16 in fluid also prevents air from entering into it when negative pressure prevails in bore 69. The fluid can be supplied by the syringe 62 or by a saline bag that is slightly pressurized above the patient's blood pressure (not shown).

Electrical wires 63, 63', 64 and 64' connect the motor 50 to a battery 65 through a four position switch 66 having a sliding block 68. In the position shown in FIG. 1 wire 63 is connected to wire 63' and wire 64 is connected to wire 64' causing the motor to rotate in the first direction. When the block 68 is slid upwards (in the direction of arrow 68') the wires are crossed so that wire 63 is connected to wire 64' and wire 64 is connected wire 63' causing the motor to rotate in the second direction and, manually alternating between these positions, will cause the motor to rotate back and forth. When the switch is slid downwards an electronic circuit contained in a block 67 is interposed between the wires 63 and 64 to the wires 63' and 64' which automatically causes the motor to rotate back and forth (the electronic circuit which is not shown is familiar to the artisan.) In a fourth off-position (not shown) the switch disconnects the battery from the motor.

Motor 50 has a commutator which can be equipped with a disk varistor to reduce electromagnetic emissions (disk varistors are commercially available, for example, from TDK Corp., Uniondale, N.Y.) Additionally capacitors 70, 71 and 72 can be connected to a housing of the motor and wired as shown in FIG. 1. Ferrite beads (not shown) can also be disposed along the wires 63, 64 and 63', 64' to further reduce the electromagnetic emissions.

A syringe 80 is connected through an introducer 75 to the vessel and can be used for the introduction of a fluid mixture comprising for example saline, heparin, a contrast agent and antispasmodic drug into the vessel. This fluid mixture can make up for the volume that is aspirated through the rotary catheter and can be used to prevent blood from entering the introducer and clotting therein. Alternatively the syringe 80 can be used to withdraw fluid and particles out of the vessel especially while the rotary catheter 10 is not disposed in the introducer. In cases where the target obstruction 11 is distant from the puncture site, a conventional guiding catheter (not shown) may be disposed in the introducer, to guide the rotary catheter 10 more definitively to the obstruction. Alternatively a specialized guiding catheter 77 with a toroidal shaped balloon 78 can be used to also seal flow through the vessel and reduce the likelihood of escapement of particles into the blood stream. The balloon 78 is inflatable and deflatable through a channel 79, defined in a wall of the guiding catheter, by a syringe 81 that is connected to the channel 79. A syringe 82 can be used to inject fluid mixture through the guiding catheter into the vessel. This fluid can make up for the volume that is aspirated through the rotary catheter and serve to suspend the obstruction particles and it prevents blood from entering the guiding catheter and clotting therein. However, syringe 82 can also be used to aspirate fluid and particles out of the vessel especially while the rotary catheter 10 is not disposed in it (while syringes 62, 80, 81 and 82 are illustrated as being connected directly to various other components it is understood that they can be connected through flexible conduits similar to flexible conduit 48.) It can be noted that syringe 82 or syringe 80 can be replaced with a bag containing a fluid mixture preferably under pressure slightly higher than the patient's blood pressure.

The guidewire 15 can be a conventional guidewire or it can be equipped with a distal particle barrier such as a filter (not shown) or a balloon 85 that is selectively inflatable through the guidewire 15 (such guidewires with balloons are commercially available from Medtronic Co., Minneapolis, Minn.)

Bodily vessels are often curved and bias a catheter that is inserted into them towards the wall of the vessel. Absent a correction mechanism, such a bias would lead tunneling catheters (i.e., catheters that are intended open an obstruction) to begin tunneling into the obstruction adjacent to the wall especially in a case of an obstruction that totally blocks the vessel and can not be crossed by the guidewire. In such a case the rotary catheter 10 can be delivered to the vicinity of the obstruction site over the guidewire which is then withdrawn proximally past the distal tip 36 of the tip. Then, as the tip rotates and the crown 27 atraumatically slides against the wall of the vessel it displaces the distal end 36 of the tip away from the wall (please note FIG. 2) urging the distal end of the tip to start tunneling away from the wall. After the total obstruction has been passed the guidewire is advanced distally beyond the obstruction and it can be left inside the vessel after the rotary catheter has been withdrawn to provide guidance to subsequent procedures such as angioplasty and stenting. It can be understood by the artisan that this correction mechanism would not work if the flexible hollow shaft 14 would have hypothetically extended beyond the tip distally as the tip could not have remotely prevented such a distal extension of the flexible hollow shaft from tunneling adjacent to the wall. Such a distal extension of the hollow shaft would have also increased the force that would have developed between the rotating crown and the wall of the vessel because, as would be appreciated by the artisan, substantially more force has to be applied at a mid point of a beam that is supported at both of its ends as compared with the force that has to applied to the one end of a cantilevered beam in order to cause the same deflection.

Figure 3A:
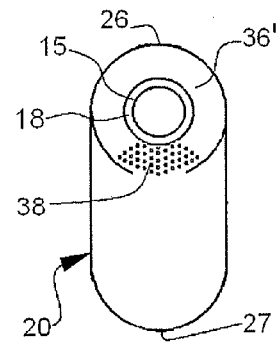
FIG. 3a shows a distal end of a modified tip.

A distal tip 36' with an enhanced ability to start tunneling has a small area of rough surface 38 on the part of the distal end of the tip that is further away from the base 26 (please note FIG. 3a) to reduce the likelihood that the small area of rough surface will come into contact with the vessel. To prevent, or to release, fibers and the like from wrapping around the hollow shaft or the tip, the hollow shaft and tip can be rotated backwards or back and forth in directions 40 and 41. Additionally, sliding the flexible tube 13 back and forth relative to the hollow shaft 14 can be used to dislodge obstruction particles and fibers that clog the flexible tube as well as to adjust and optimize the aspiration.

The rotary catheter can be introduced into the vessel directly, when the vessel is surgically accessed, or percutaneously through an introducer 75, having a sheath 76. The size of an allowable puncture wound 12' in the vessel wall limits the diameter of the sheath 76 and which limits an outside diameter 13od of the flexible tube 13 and this in turn limits the size of the inner workings of the catheter and of the tip 20. The flexible tube's internal diameter 13id and an outside diameter 14od of the hollow shaft 14 (please note FIG. 8) define between them an aspiration channel 87. To maximize the cross sectional area of the aspiration channel 87 and the size a particle 87' that the aspiration channel can ingest, the sheath 76 as well as the flexible tube 13 are preferably made of a thin plastic materials and a diameter 14od of the hollow shaft is kept substantially smaller than the diameter 13id. The distal end of the hollow shaft 14 extends out of a distal end of the flexible tube 13 and is free to move radially in the channel, to one side or another, enabling the channel to ingest particles whose diameter (assuming they are round) is as large as, or smaller, than a difference between the diameters 13id to 14od. It should be noted that, if the distal end of the hollow shaft 14 was mechanically connected to and centered in the distal end of the flexible tube 13, for example by a bearing, the diameter of particles that could have theoretically enter the channel 87 would have been reduced by ½ and their weight by ⅞. As the tip rotates the interaction of the tip with its surroundings and dynamic forces may cause the distal end of the hollow shaft to randomly move radially or vibrate in the channel which further impedes particles from clogging the aspiration channel (again, by comparison, if the distal ends of the hollow shaft and the flexible tube were mechanically connected by a bearing or the like, not only could such a connection interfere with flow through the channel it would also diminish the vibratory unclogging action referred to above.) It can also be noted that the lack of mechanical connection between the distal ends of the flexible tube 13 and the hollow shaft 14 enhances the flexibility of the rotary catheter by allowing slight longitudinal relative movement between the flexible tube 13 and the hollow shaft 14 when the catheter is bent.

If however an oversized particle (which measures across more than the difference between the diameters 13id to 14od) does enter and wedges in the channel 87 the spiraled wire 17 (if one is used) is preferably rotated in a direction that conveys it distally to prevent from such oversized particles from accumulating and clogging the aspiration channel. This action can be bolstered by making the cross section of the wire (from which the spiraled wire is made) with small external ridges 34 (please note FIG. 5). However, particles that are small enough not to become wedged in the channel 87 are practically unaffected by the small ridges 34 and are readily aspirated proximally, eased by the relative rotation of the hollow shaft 14 to the flexible tube 13 which substantially reduces the frictional resistance to the movement of particles through the channel 87 thus, the combined relative rotary and radial motion between the hollow shaft and the flexible tube ease the movement of particles into and through the aspiration channel and impedes particles from clogging it.

Figure 3:
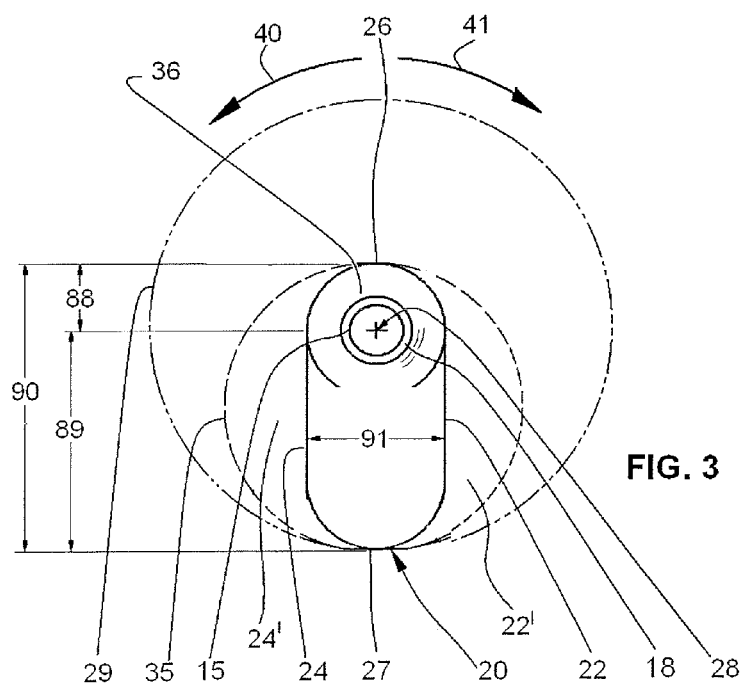
FIG. 3 shows a distal end of the tip viewed on plane 3-3 marked on FIG. 2.

It can also be appreciated that enlarging the tip's height 90 to closely fit through the introducer enhances the radial reach 89 of the tip and the cross-sectional area of the tunnel that the tip opens through the obstruction (please note FIG. 3). Increasing the tip height 90 beyond the flexible tube's internal diameter 13id (please note FIG. 8) allows the flexible tube to be advanced to the tip but not over it. The tip's height can be reduced so it is slightly smaller than the internal diameter 13id allowing the flexible tube to be advanced over it and shield it (please note FIGS. 10a, 10b.) In this shielded mode the rotary catheter can readily aspirate soft obstructions that do not have to be broken down prior to entering the flexible tube because the tip's narrowed cross-section leaves open aspiration passageways 22' and 24' between tip's sides 22 and 24 to the flexible tube's wall, respectively. As the soft obstruction enters the passageways 22' and 24' and gets in between the rotating tip's sides and the flexible tube's wall, the rotating tip macerates the clot so that it can be readily aspirated all the way into the syringe 37. Similarly, passageways 22' and 24' (please note FIG. 3) enable particles, such as those generated by the tip, to pass alongside the tip and be aspirated by the flexible tube 13 whenever the tip is working in a tunnel or a small vessel whose diameter is close to the tip's height 90.

Figure 11:
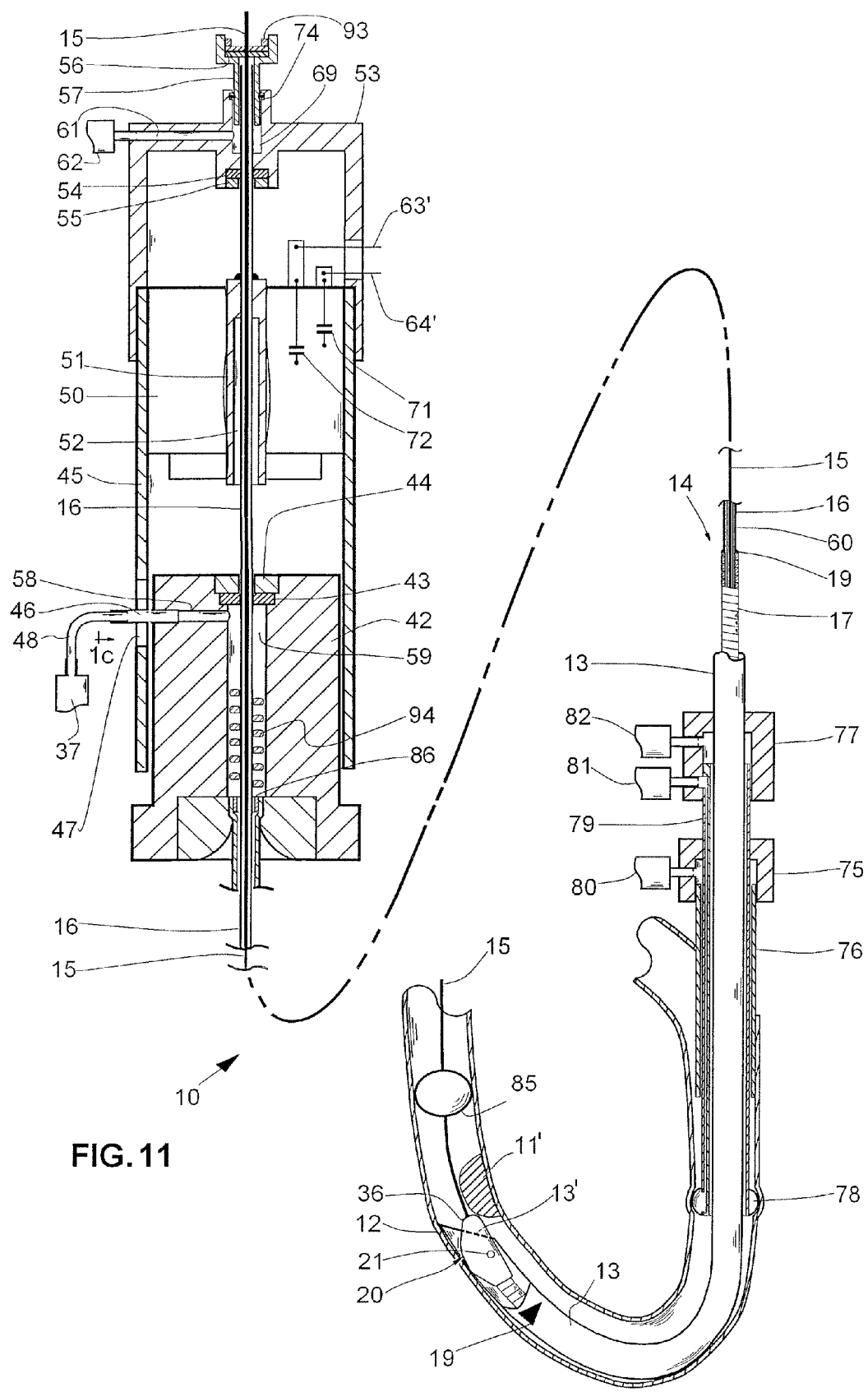
FIG. 11 shows a further modification of the rotary catheter wherein the distal end of the flexible tube is terminated diagonally.

FIG. 11 shows a further modification where the flexible tube 13 is terminated along a diagonal line 13' so that when the cylinder 42 is partially pulled out of the housing, the flexible tube partially shields the tip. As can be understood by the artisan, the length of the slot 47 can be adjusted to enable the flexible tube to move from a fully shielding position to a position where the tip and a short section of the spiral are exposed. The configuration shown in FIG. 11 enables the tip to be advanced and urged into contact with an asymmetrical obstruction 11', which is located on one side of the vessel, while the flexible tube acts as a barrier between the tip and an opposite side of the vessel. A radio-opaque marker 19, affixed to the wall of the flexible tube, can be used to assist the user in positioning the flexible tube relative to the obstruction.

Figures 12, 13:
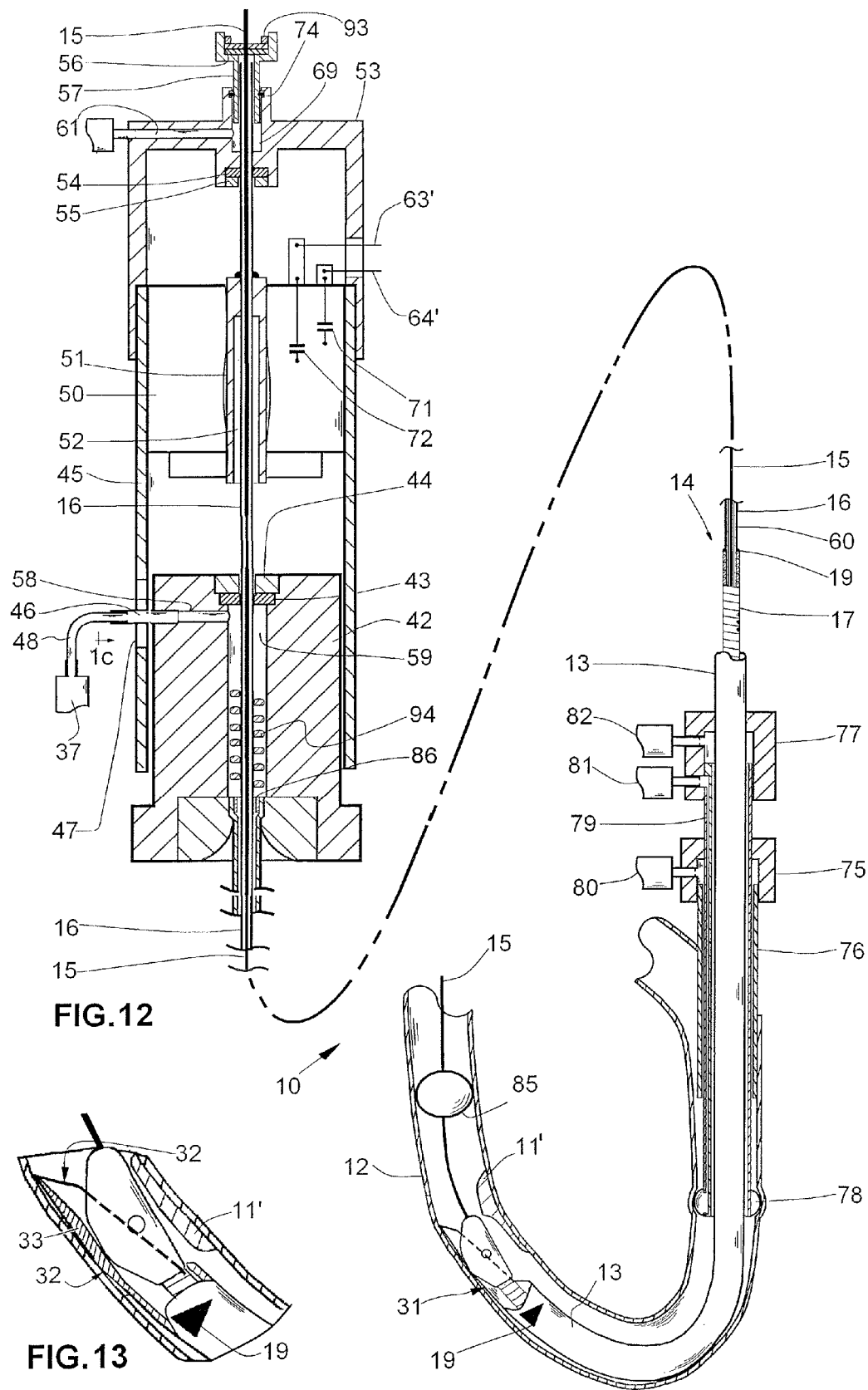
FIG. 12 shows a further modification of the rotary catheter wherein the shape of the distal end of the flexible tube resembles a scoop of a garden trowel.
FIG. 13 shows an further modification of the rotary catheter wherein the sheath resembles a scoop of a garden trowel with a thickened bottom.

FIG. 12 shows a modification of the rotary catheter of FIG. 11 where a flexible tube's distal end 31 resembles a miniaturized scoop of a gardening trowel. The scoop shields a certain length of one side of the vessel's wall from the rotating tip while urging the rotating tip towards an asymmetrical obstruction 11' located on the opposite side of the wall. FIG. 13 shows a scoop 32 with a thicker bottom 33 to urge the tip further towards the obstruction. The elongated shape of scoops 31 and 32 shields a length of the obstruction without having to re-position the scoop in the vessel.

FIG. 1a shows the rotary catheter 10 with the flexible tube 13 slid distally, relative to the hollow shaft 14 and the tip 20, to reduce a gap between an edge 13e of the flexible tube and the tip. The reduced gap impedes the edge 13e from engaging with the wall of the vessel 12. While the edge 13e is preferably rounded or chamfered (please note FIG. 8) the reduced gap further reduces the likelihood that the edge 13e would scrap the wall of the vessel 12 while the rotary catheter is advanced distally in the vessel.

While the present invention has been illustrated with specific embodiment it should be understood that modifications and substitutions may be made within the spirit of the invention and the scope of the claims. For example, the hollow shaft portion 16 can be made to constitute the majority or all of the length of the hollow shaft 14. Conversely, to enhance the flexibility of the rotary catheter, the portion 17 (or a cable tube of the type made by the previously mentioned Asahi Intecc Co.) can be lengthened to constitute the majority or all of the length of the hollow shaft 14. A further modification of the hollow shaft 14 is to have a first short proximal tube portion which is connected to a second proximal spiraled wire portion which is connected to a distal tube portion which is connected to a fourth distal spiraled wire portion. Such a configuration may be useful in a longer rotary catheter needed to reach the heart region from a typical vascular entry point at the groin region. In such an application the proximal spiraled wire portion provides enhanced flexibility at the entry region, whereas, the distal spiraled wire portion provides enhanced flexibility needed in the heart region while the third proximal tube portion is sufficiently flexible to be disposed in between these regions (in the relatively straight aorta.) Such staggered construction reduces the system's bulk and the longitudinal flexibility of the hollow shaft 14.

The sides 22 and 24 can be made slightly curved or tilted (please note FIG. 16) from the parallel position depicted in FIG. 3, so as to increase the passages 22' and 24' while narrowing the crown, or conversely, they be made so as to increase the crown to provide a larger bearing area for the tip as it slides over a wall of the vessel 13.

Figure 15:
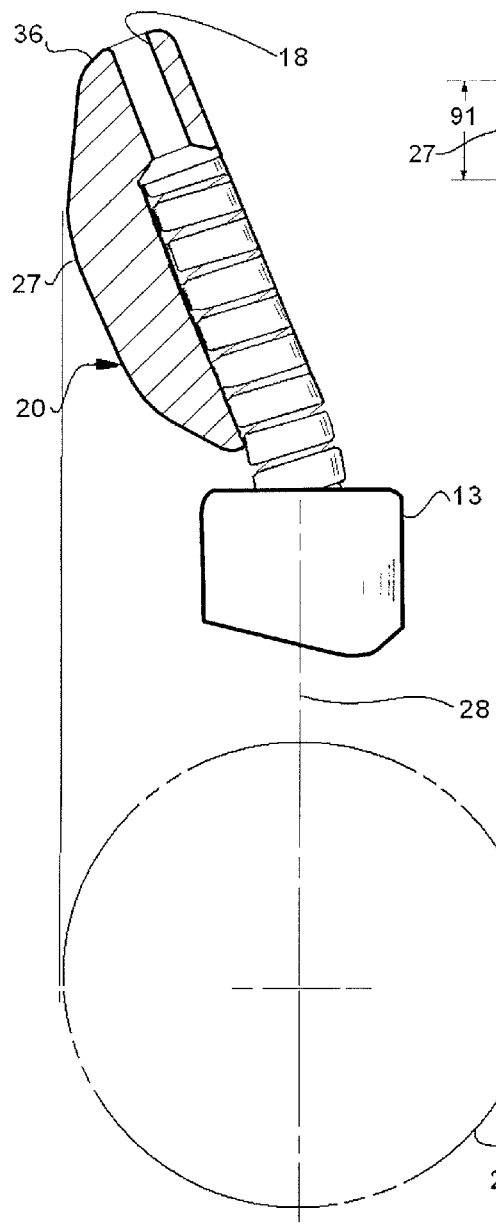
FIG. 15 shows the modified rotary catheter shown in FIG. 14 wherein the distal end section of the spiral wire automatically assumed a curved shape and increased the offset of the tip in the absence of the guidewire.
Figure 14:
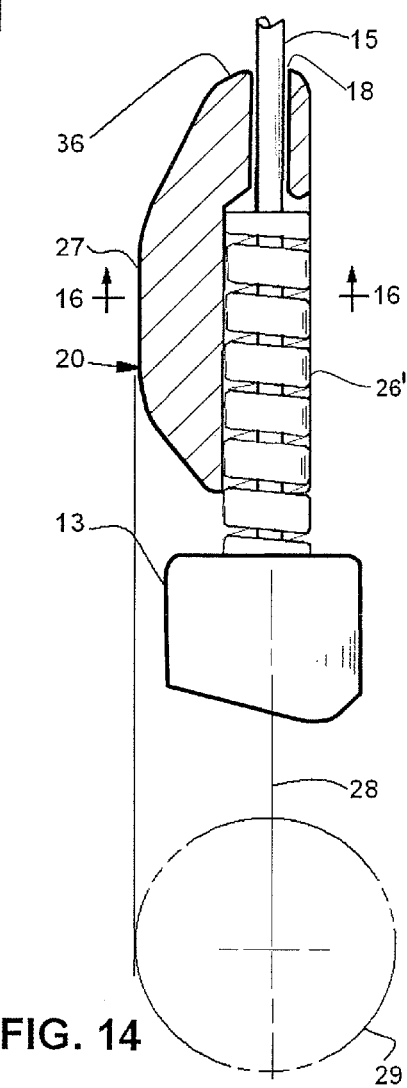
FIG. 14 shows a further modification of the rotary catheter wherein a distal end section of the spiral wire that is extended out of the distal end of the flexible tube is straightened by a guidewire that is disposed through it, but it is pre-formed to automatically assume a curved shape in response to the guidewire being withdrawn from within the distal end section of the spiral wire.

The guidewire enables delivering the rotary catheter delivering the rotary catheter through tortuous vasculature to remote occlusions and operating it with an enhanced degree of safety, however, a rotary catheter according to the present invention is adaptable to occasionally operate with the guidewire withdrawn proximally into the hollow shaft to address specific clinical scenarios. One such scenario of adapting the rotary catheter to cross total occlusion was previously discussed. A second scenario relates to treating large vessels (e.g., blood vessels in the pelvic area, hemodialysis fistula, aneurysm) with a modified rotary catheter shown in FIGS. 14-16. FIG. 14 shows a distal end section of the spiral wire 17 that extends out of the distal end of the flexible tube 13 being straightened by a guidewire 15 that is disposed through it, however, the distal end section of the spiral wire is pre-formed to automatically assume a curved shape when the guidewire 15 is withdrawn from it (please note FIG. 15) and to thereby increase the offset of the tip 20. This in turn substantially increases the area within circle 29' that the tip sweeps (please note FIG. 15) as compared to the area within circle 29 (please note FIGS. 14 and 3.) It should however be understood that the actual cross section of the tunnel that is opened by the tip will also be effected by, for example, the topography and material of the surrounding vessel and obstruction and the rotational speed of the hollow shaft and tip. Thus, when a larger segment of a vessel has to be treated the guidewire can be withdrawn proximally out of the spiraled wire, allowing the pre-formed distal end section of the spiral wire to automatically assume its pre-formed curved shape shown in FIG. 15 and thereby increase the tip's sweep. Optionally the user can gradually withdraw the guidewire to achieve a corresponding gradual curving of the distal end section of the spiral wire. After opening the large vessel the guidewire can be re-advance distally through the distal end section of the spiral wire to reassume the configuration shown in FIG. 14. After the rotary catheter has been used the guidewire may be left in the vessel for followup procedure (e.g., angioplasty and/or deployment of a stent.)

Figure 16:
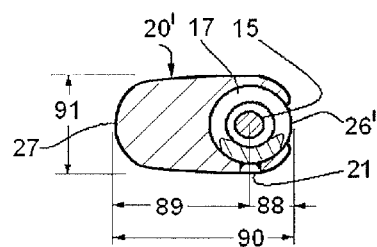
FIG. 16 is cross sectional view of the tip, along a plane 16-16 marked on FIG. 14, which shows a further modification of the tip wherein an offset of the base is minimized and an offset of the crown is enhanced.

FIG. 16 is cross sectional view of a modified tip 20', along a plane 16-16 marked on FIG. 14. The tip has slightly curved sides and an enhanced offset 89 which achieved by reducing the offset 88 and essentially using the spiraled wire as a base 26'.

The invention claimed is:

1. A rotary catheter for opening an obstruction in a bodily vessel, comprising in combination;
a motor-driven flexible hollow shaft rotatably disposed in a flexible tube, an aspiration channel defined between an internal diameter of said flexible tube and an external diameter of said hollow shaft, at least a distal portion of said hollow shaft being free to move radially in said aspiration channel enabling said aspiration channel to ingest particles which are as large as, or smaller, than a difference between said internal and external diameters, relative motion between said rotating hollow shaft and said flexible tube eases movement of the particles through said aspiration channel and impedes the particles from clogging said aspiration channel,
a tip having a narrowed cross section and affixed to a terminal distal end of said hollow shaft, said tip having a rounded terminal distal end which defines a bore adapted to fit over a guidewire, said hollow shaft and said tip being rotatable and slideable over said guidewire, said tip also having a first flattened side and a second flattened side opposite said first flattened side, said first flattened side adapted to impact said obstruction when said tip rotates in a first direction, said first flattened side and said second flattened side being a cross sectional distance apart to define a width of said tip transverse to a longitudinal axis of said tip, said tip also having a base and an opposing crown that is adapted to atraumatically slide against a wall of said vessel as said tip rotates outside of said flexible tube, said base and said opposing crown defining the height of said tip by a cross sectional distance transverse to a longitudinal axis of said tip, said crown being offset away from a longitudinal axis of said hollow shaft further than said base is offset away from said longitudinal axis, said cross sectional distance between said flattened sides being smaller than said cross sectional distance between said crown and said base and wherein a widest portion of said width is defined by said flattened sides.

2. The rotary catheter as in claim 1, wherein at least a distal portion of said hollow shaft comprises a spiraled wire.

3. The rotary catheter as in claim 2, wherein said spiraled wire is rotated in a direction that said spiraled wire mechanically conveys oversized particles distally.

4. The rotary catheter as in claim 1, wherein said guidewire can be withdrawn proximally beyond a terminal distal end of said tip and said rotating crown slides against said wall of said vessel and displaces said distal end of said tip away from said wall of said vessel.

5. The rotary catheter as in claim 1, wherein a distal end section of said hollow shaft is extended out of said distal end of said flexible tube and is pre-formed to automatically attempt to assume a curved shape and increase an offset of said tip in response to said guidewire being withdrawn from within said distal end section of said hollow shaft.

6. The rotary catheter as in claim 1, wherein said hollow shaft is rotatable, back and forth, in said first direction and a second direction of rotation.

7. The rotary catheter as in claim 6, wherein said second flattened side is adapted to impact said obstruction when said hollow shaft is rotated in said second direction.

8. The rotary catheter as in claim 1, wherein said flexible tube is slideable relative to said hollow shaft.

9. The rotary catheter as in claim 1, wherein said flexible tube is slid distally, relative to said hollow shaft, to reduce a gap between an edge of said flexible tube and said tip to impede said edge from engaging with said wall of said vessel while said rotary catheter is advanced distally in said vessel.

10. The rotary catheter as in claim 1, wherein said flexible tube can be selectively slid distally or proximally, relative to said hollow shaft, to shield said tip or to extend it out of said distal end of said flexible tube, respectively.

11. The rotary catheter as in claim 2, wherein a flexible guidewire liner is disposed at least in a distal portion of said spiraled wire.

12. The rotary catheter for opening an obstruction in a bodily vessel as in claim 1, wherein said aspiration channel is connected to a suction means through a bore in which a closely fitting spiral, affixed to said hollow shaft, is rotatably disposed and adapted to automatically enable movement of fluid and particles when said hollow shaft and said spiral rotate and to automatically resist said movement when said hollow shaft and said spiral are at rest.

13. The rotary catheter for opening an obstruction in a bodily vessel as in claim 1, said hollow shaft is adapted to rotate and slide over a guidewire,
wherein a proximal portion of said hollow shaft is a thin walled tube nested in and power transmittingly connected to an output shaft of said motor,
said thin walled tube rotatably passing through a seal set comprising a bearing and an adjacent seal, said bearing elastically deflecting said thin walled tube as needed to align it with said seal.

14. The rotary catheter as in claim 13, wherein said thin walled tube also passing through a second seal set that is located proximally to said first seal set, said second seal set comprising a bearing and an adjacent second seal, said bearing aligning said thin walled tube with said seal.

15. The rotary catheter as in claim 14, having a sliding housing means which houses said second seal set and a seal that is located proximally to said second seal set, enabling said seal to slide onto a proximal end of said thin walled tube and expose a proximal open end of said thin walled tube, or alternatively to slide proximally, off said proximal end of said thin walled tube, and to seal around said guidewire.

16. A method of opening an obstructed bodily vessel comprising the following steps:
inserting into said vessel a guidewire through the obstruction,
sliding over said guidewire a motor-driven flexible hollow shaft with a tip having a narrowed cross section, said tip affixed to a terminal distal end of said hollow shaft, said hollow shaft and tip being rotatably disposed in a flexible tube with an aspiration channel defined between said hollow shaft and said flexible tube, said tip having a rounded terminal distal end, flattened sides a cross sectional distance apart to define a width of said tip transverse to a longitudinal axis of said tip, a base and an opposing crown that is offset away from a longitudinal axis of said hollow shaft further than said base, said base and said opposing crown defining the height of said tip by a cross sectional distance transverse to a longitudinal axis of said tip, said cross sectional distance between said flattened sides being smaller than said cross sectional distance between said crown and said base leaving open aspiration passages alongside said tip, wherein a widest portion of said width is defined by said flattened sides,
rotating said hollow shaft and tip causing said tip to penetrate and impact the obstruction while aspirating out of said vessel, through said aspiration channel, particles suspended in fluid.

17. A method of opening a totally obstructed bodily vessel comprising the following steps:
inserting into said vessel a guidewire to the obstruction,
sliding over said guidewire a motor-driven flexible hollow shaft with a tip having a narrowed cross section, said tip affixed to a terminal distal end of said hollow shaft, said hollow shaft being rotatably disposed in a flexible tube with an aspiration channel defined between said hollow shaft and said flexible tube, said tip having a rounded terminal distal end, flattened sides a cross sectional distance transverse to a longitudinal axis of said tip apart to define a width of said tip, a base and an opposing crown that is offset away from a longitudinal axis of said hollow shaft further than said base, said base and said opposing crown defining the height of said tip by a cross sectional distance transverse to a longitudinal axis of said tip, said cross sectional distance between said flattened sides being smaller than said cross sectional distance between said crown and said base leaving open aspiration passages alongside said tip, wherein a widest portion of said width is defined by said flattened sides,
with said guidewire being proximal to said terminal distal end of said tip, rotating said hollow shaft and tip causing said tip to tunnel through said obstruction.

18. A method of opening an obstructed bodily vessel with a large diameter comprising the following steps:
inserting into said vessel a guidewire to or through the obstruction, sliding over said guidewire a motor-driven flexible hollow shaft with a tip having a narrowed cross section, said tip affixed to a terminal distal end of said hollow shaft, said hollow shaft being rotatably disposed in a flexible tube with an aspiration channel defined between said hollow shaft and said flexible tube, said tip having a rounded terminal distal end, flattened sides a cross sectional distance transverse to a longitudinal axis of said tip apart to define a width of said tip, a base and an opposing crown that is offset away from a longitudinal axis of said hollow shaft further than said base, said base and said opposing crown defining the height of said tip by a cross sectional distance transverse to a longitudinal axis of said tip, said cross sectional distance between said flattened sides being smaller than said cross sectional distance between said crown and said base leaving open aspiration passages alongside said tip, wherein a widest portion of said width is defined by said flattened sides,
wherein a distal end section of said hollow shaft is extended out of said distal end of said flexible tube and is pre-formed to automatically assume a curved shape and increase an offset of said tip in response to said guidewire being withdrawn from within said distal end section of said hollow shaft,
advancing said rotary catheter over said guidewire until said tip reaches said large diameter vessel,
withdrawing said guidewire proximally enabling said distal end section of said hollow shaft to assume a curved shape,
rotating said hollow shaft and tip and impacting the obstruction while aspirating out of said vessel, through said aspiration channel, particles suspended in fluid.

19. The rotary catheter for opening an obstruction in a bodily vessel as in claim 1, wherein said flattened sides are parallel, slightly curved or tilted.

\* \* \* \* \*